(12) United States Patent
Kim et al.

(10) Patent No.: US 8,870,456 B2
(45) Date of Patent: Oct. 28, 2014

(54) OPENING AND CLOSING MODULE, CONTROL METHOD FOR THE SAME, IMAGING APPARATUS USING THE SAME

(75) Inventors: Duck-june Kim, Ansan-si (KR); Sang-hoon Ji, Seoul (KR); Woong-hee Shon, Seongnam-si (KR); Sang-moo Lee, Yongin-si (KR); Kyung-tae Nam, Ansan-si (KR); Kwang-hee Lee, Anyang-si (KR)

(73) Assignee: Korea Institute of Industrial Technology, Chungcheongnam-do (KR)

( * ) Notice: Subject to any disclaimer, the term of this patent is extended or adjusted under 35 U.S.C. 154(b) by 856 days.

(21) Appl. No.: 12/957,061

(22) Filed: Nov. 30, 2010

(65) Prior Publication Data

US 2011/0316538 A1 Dec. 29, 2011

(30) Foreign Application Priority Data

Jun. 29, 2010 (KR) ........................ 10-2010-0062278

(51) Int. Cl.
*H05G 1/04* (2006.01)
*H05G 1/02* (2006.01)
*A61B 6/00* (2006.01)

(52) U.S. Cl.
CPC .................................. *A61B 6/4435* (2013.01)
USPC ............................................ 378/193; 378/204

(58) Field of Classification Search
CPC .................. A61N 5/01; A61N 5/1081; A61N 2005/0632; A61N 2005/0633; H05G 1/04; H05G 1/02
USPC ............. 378/193–198, 204, 210; 250/370.09, 250/522.1
See application file for complete search history.

(56) References Cited

U.S. PATENT DOCUMENTS 6,940,941 B2 * 9/2005 Gregerson et al. ................ 378/4

* cited by examiner

*Primary Examiner* — Anastasia Midkiff
(74) *Attorney, Agent, or Firm* — Rabin & Berdo, P.C.

(57) ABSTRACT

An imaging apparatus includes: a rotator having a shape of a perforated circular plate and rotating around a rotating axis of a center of the perforated circular plate; and a supporter having a perforated circular plate and one side of which is connected to one side of the rotator such that the rotator is restricted only to rotation movement. The supporter includes a supporter opening/closing part a part of which is separated along the rotating axis and then rotates by a predetermined angle around the rotating axis, and the rotator includes a rotator opening/closing part a part of which integrally moves with the supporter opening/closing part.

15 Claims, 10 Drawing Sheets

OPENING AND CLOSING MODULE, CONTROL METHOD FOR THE SAME, IMAGING APPARATUS USING THE SAME

CROSS-REFERENCE TO RELATED APPLICATION

This application claims priority to and the benefit of Korean Patent Application No. 10-2010-0062278 filed in the Korean Intellectual Property Office on Jun. 29, 2010, the entire contents of which are incorporated herein by reference.

BACKGROUND OF THE INVENTION (a) Field of the Invention

The present invention relates to an opening and closing module, a control method for the same, and an imaging apparatus using the same which can take multi-dimensional imaging.

(b) Description of the Related Art

An imaging apparatus including an O-shaped gantry ring in which a hollow space is provided, and a C-shaped rotor which is disposed with the gantry ring so as to be rotatable in 360 degrees independently from the gantry ring has been introduced.

Such a conventional imaging apparatus is configured that a segment of the gantry ring is separable so that object (generally a patient) can be easily moved to the center portion of the gantry ring under various conditions. If the segment of the gantry ring is separated, an O-shaped gantry ring is converted into a C-shape. At this time, the rotor is disposed such that the gantry ring and the C shape are corresponding to each other (i.e., open parts are coincided), the imaging object can be easily moved to the center part of the gantry ring.

After setting the imaging object, the separated segment is re-coupled to the gantry ring, so the gantry ring becomes an O shape, and the C-shaped rotor rotates along a rail which is provided in the gantry ring, and thereby two-dimensional or three-dimensional imaging can be performed.

However, since the rotor is formed with a non-symmetrical C shape, there is a problem in that vibrations may occur during rotation thereof. In addition, the rotor is disposed in the gantry ring and only the rotor rotates apart from the gantry ring, so space occupied by the imaging apparatus becomes larger.

SUMMARY OF THE INVENTION

The present invention has been made in an effort to provide an imaging apparatus in which vibration during rotation can be reduced and an imaging object can be easily set.

Further, the present invention has also been made in an effort to provide an imaging apparatus a size of which is substantially reduced, so room for an imaging object can be increased.

An exemplary imaging apparatus according to an embodiment of the present invention includes: a rotator having a shape of a perforated circular plate and rotating around a rotating axis of a center of the perforated circular plate; and a supporter having a perforated circular plate and one side of which is connected to one side of the rotator such that the rotator is restricted only to rotation movement. The supporter includes a supporter opening/closing part a part of which is separated along the rotating axis and then rotates by a predetermined angle around the rotating axis, and the rotator includes a rotator opening/closing part a part of which integrally moves with the supporter opening/closing part.

The rotator opening/closing part may be a portion corresponding to a range of predetermined angle in a circumferential direction in the rotator, and the supporter opening/closing part may be a portion in the supporter corresponding to the rotation opening/closing part.

The supporter may further include a supporter fixing part which forms the perforated circular plate together with the supporter opening/closing part before the supporter opening/closing part is separated along a direction of the rotating axis. The rotator may further include a rotator fixing part which forms the perforated circular plate shape together with the rotator opening/closing part before the rotator opening/closing part is separated along a direction of the rotating axis.

The rotator may further include a source emitting light and a detector receiving the light, and the source and the detector are arranged to face each other such that the rotating axis is disposed at the center therebetween.

The rotator may include a rotating gear which is formed on an outer circumference thereof along a circumferential direction.

The supporter may further include a rotating motor which is engaged with the rotating gear to rotate the rotator around the rotating axis.

The supporter may further include a rotating guide which is formed on the other side thereof along a circumferential direction such that the rotator can rotate around the rotating axis. The rotator may further include a guide roller which is provided at one side thereof along a circumferential direction corresponding to the rotating guide.

The supporter may further include a manipulator connecting part which is connected to a manipulator which controls linear or rotational movement in space.

The supporter may further include an opening/closing module which separates and rotates the supporter opening/closing part.

The opening/closing module may include a lifting part which separates the supporter opening/closing part along a direction of the rotating axis, and a rotating part which rotates the supporter opening/closing part by a predetermined angle around the rotating axis.

The rotating part may include an opening/closing guide which is formed at one side of the supporter fixing part along a circumferential direction, and a moving member which moves along the opening/closing guide. The lifting part may include a guide rod which protrudes from the moving member along a direction of the rotating axis, and a connecting member one end of which is connected to one side of the supporter opening/closing part and the other end of which is penetrated so as to be moved along a longitudinal direction of the guide rod.

The moving member may include an opening/closing gear which is formed on an outer circumference or an inner circumference along a circumferential direction.

The rotating part may further include an opening/closing motor which is engaged with the opening/closing gear to urge the moving part to move along the opening/closing guide.

The lifting part may further include an air cylinder which moves the connecting member along a longitudinal direction of the guide rod.

An exemplary opening/closing module according to an embodiment of the present invention includes: a lifting part which separates an opening/closing part along a direction of a rotating axis; and a rotating part which rotates the opening/closing part by a predetermined angle around the rotating axis.

The rotating part may include an opening/closing guide which is formed at one side of a fixing part along a circumferential direction, and a moving member which moves along the opening/closing guide. The lifting part may include a guide rod which protrudes from the moving member along a direction of the rotating axis, and a connecting member one end of which is connected to one side of the opening/closing part and the other end of which is penetrated so as to be moved along a longitudinal direction of the guide rod.

The moving member may include an opening/closing gear which is formed on an outer circumference or an inner circumference along a circumferential direction.

The rotating part may further include an opening/closing motor which is engaged with the opening/closing gear to urge the moving part to move along the opening/closing guide.

The lifting part may further include an air cylinder which moves the connecting member along a longitudinal direction of the guide rod.

According to an exemplary embodiment of the present invention, a control method for an opening/closing module for controlling an opening/closing module including a lifting part which separates an opening/closing part along a direction of rotating axis, and a rotating part which rotates the opening/closing part around a rotating axis includes: separating the opening/closing part in a direction of rotating axis by the lifting part; and rotating the separated opening/closing part by a predetermined angle around the rotating axis by the rotating part.

The rotating part may include an opening/closing guide which is formed at one side of a fixing part along a circumferential direction, and a moving member which moves along the opening/closing guide. The lifting part may include a guide rod which protrudes from the moving member along a direction of the rotating axis, and a connecting member one end of which is connected to one side of the opening/closing part and the other end of which is penetrated so as to be moved along a longitudinal direction of the guide rod.

The moving member may include an opening/closing gear which is formed on an outer circumference or an inner circumference along a circumferential direction, the rotating part may further include an opening/closing motor which is engaged with the opening/closing gear to urge the moving part to move along the opening/closing guide, and the lifting part may further include an air cylinder which moves the connecting member along a longitudinal direction of the guide rod.

The separating may be moving the connecting member which is connected to the opening/closing part via an air cylinder along a longitudinal direction of the guide rod so as to separate the opening/closing part in a direction of rotating axis, and the rotating may be that the opening/closing part rotates together with the guide rod and the connecting member while the moving member moves along the opening/closing guide by the operation of the opening/closing motor which is engaged with the opening/closing gear.

DETAILED DESCRIPTION OF THE EMBODIMENTS

Exemplary embodiment of the present invention will hereinafter be described in detail with reference to the drawing.

The present invention relates to an imaging apparatus taking a two-dimensional or a three-dimensional image during rotation, and more particularly to an imaging apparatus which is provided with a symmetrical rotator in order to decrease vibrations during rotation for taking images.

Figure 1:
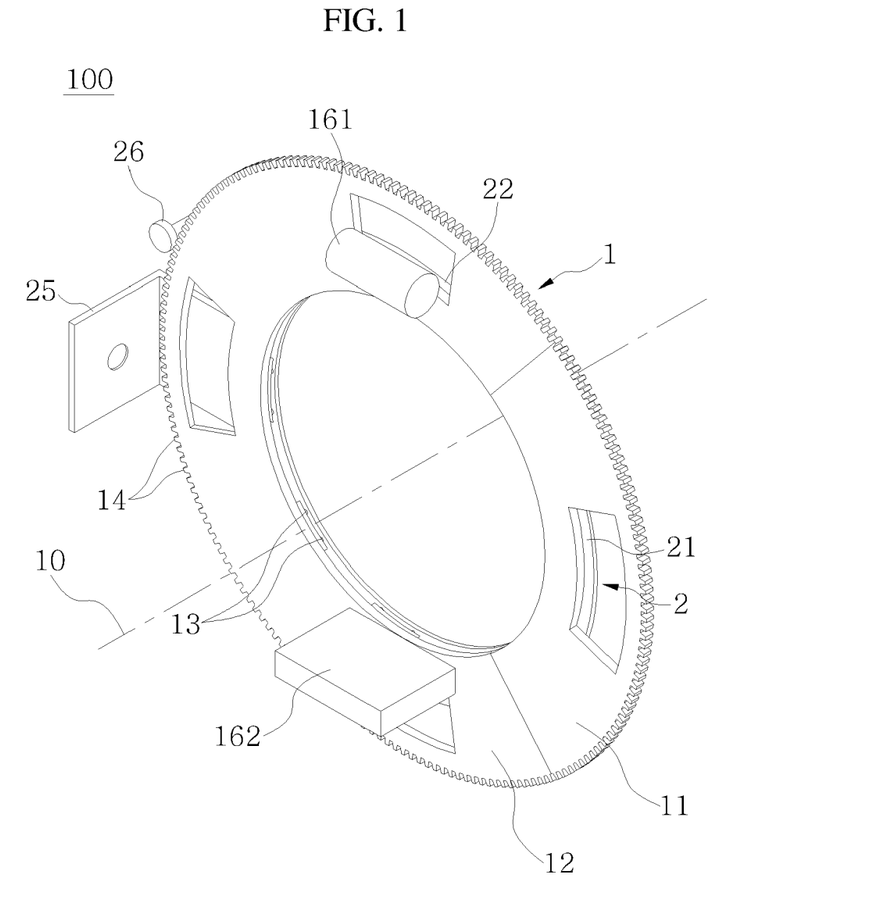
FIG. 1 is a frontal perspective view of an imaging apparatus according to an embodiment of the present invention.
Figure 2:
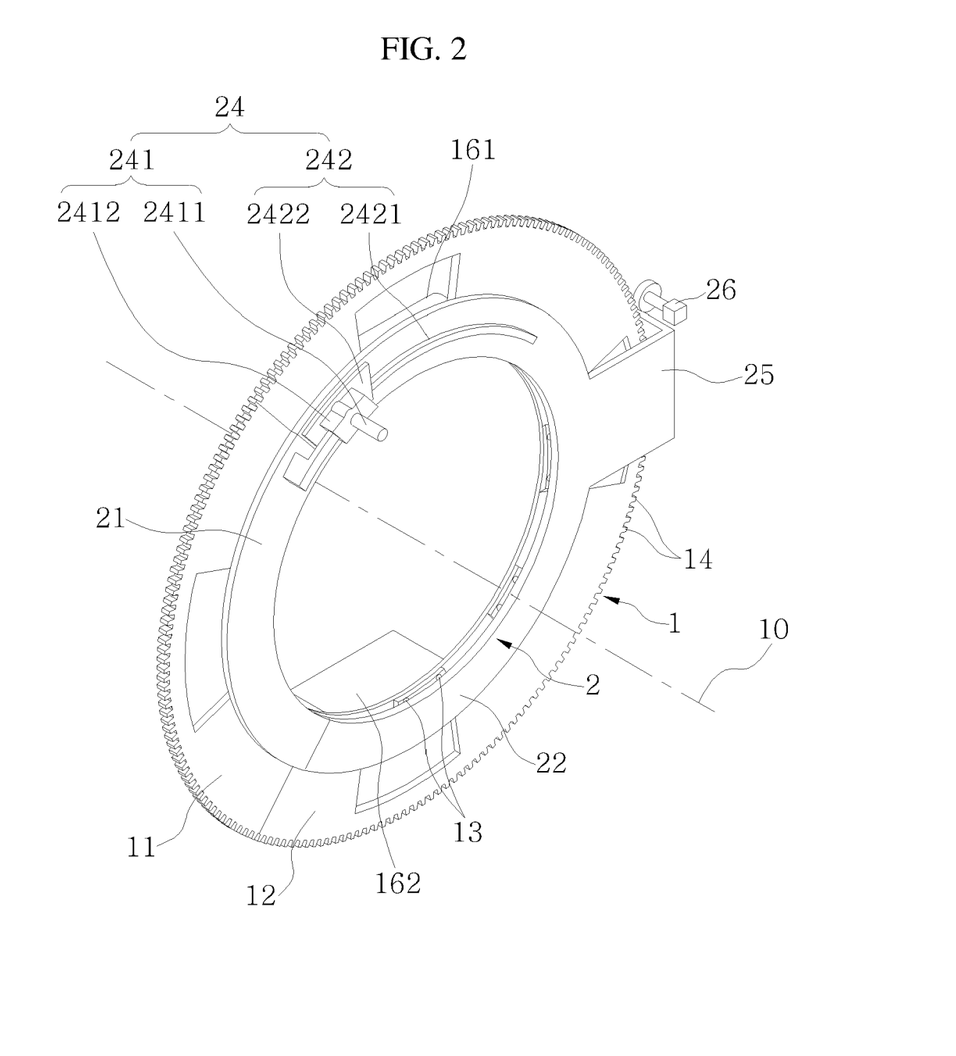
FIG. 2 is a rear perspective view of an imaging apparatus of FIG. 1.
Figure 3:
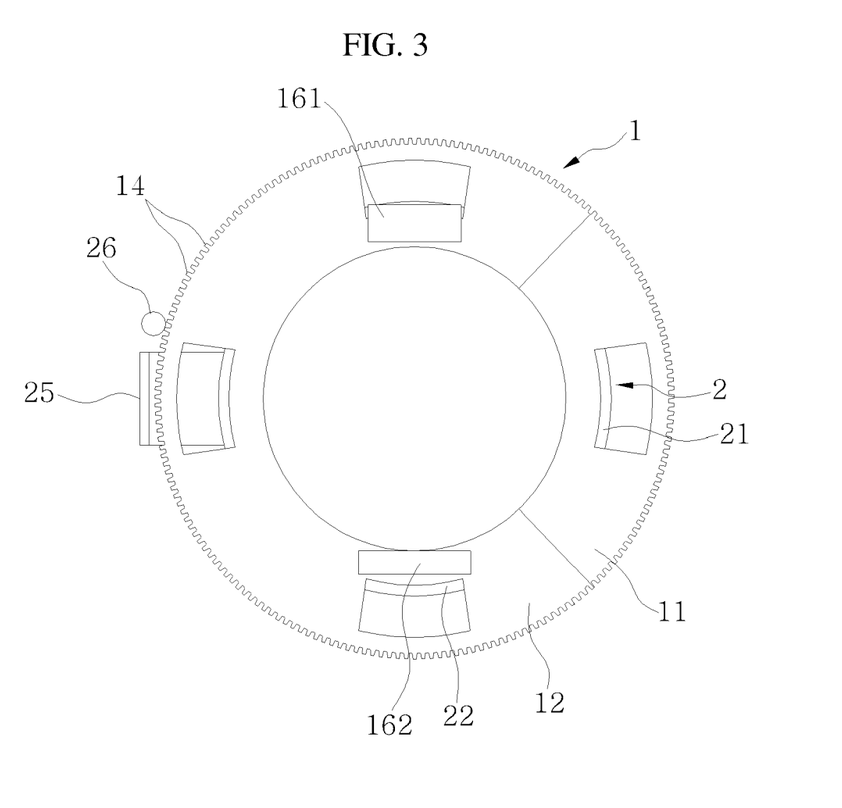
FIG. 3 is a front elevational view of an imaging apparatus of FIG. 1.
Figure 4:
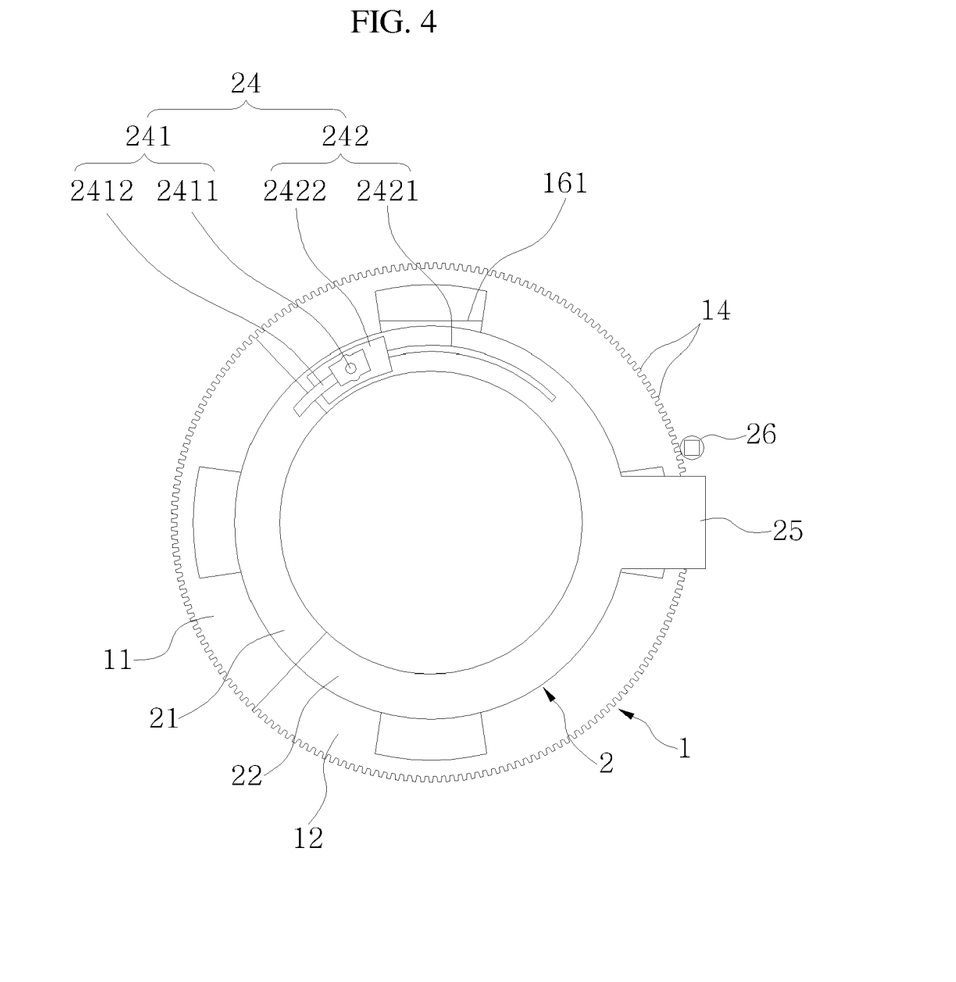
FIG. 4 is a rear elevational view of an imaging apparatus of FIG. 1.

FIG. 1 is a frontal perspective view of an imaging apparatus according to an embodiment of the present invention, FIG. 2 is a rear perspective view of an imaging apparatus of FIG. 1, FIG. 3 is a front elevational view of an imaging apparatus of FIG. 1, and FIG. 4 is a rear elevational view of an imaging apparatus of FIG. 1.

Referring to FIG. 1 to FIG. 4, an imaging apparatus 100 according to an embodiment of the present invention includes a rotator 1 and a supporter 2.

First, rotator 1 will be described.

As shown in FIG. 1 to FIG. 4, rotator 1 has a shape of a perforated circular plate and rotates around a rotating axis 10 of a center of the perforated circular plate. For example, the shape of the perforated circular plate may be a shape of a circular plate which is perforated at a center portion thereof with a circle shape, a shape of alphabet O, a shape of a donut, or a shape of a ring.

Further, rotator may be configured such that it can be able to rotate only around rotating axis 10 in a state that degree of freedom for linear or rotational movement in other direction of the rotator 1 is restricted by supporter 2. Further detailed description for this will be made later while describing supporter 2.

As shown in FIG. 1 to FIG. 4, rotator 1 includes a rotator opening/closing part 11 which moves integrally with a supporter opening/closing part 21. For example, rotator opening/closing part 11, which is a portion of rotator 1, may be a portion corresponding to a range of a predetermined angle in a circumferential direction in rotator 1. That is, a portion of rotator 1, which is rotator opening/closing part 11, may be a portion corresponding to a region within a predetermined angle in a circumferential direction of perforated circular plate. Referring to FIG. 3 and FIG. 4, rotator opening/closing part 11 may be a portion corresponding to a region within about 90 degrees in a circumferential direction of perforated circular plate.

At this time, the predetermined angle can be varied depending on surrounding conditions. However, it is preferable to determine the predetermined angle considering object of the present invention of making movement of setting of by opening the side of imaging apparatus 100 (that is, converting shape of rotator 1 and supporter 2 from O-shape to C-shape)

by integrally moving rotator opening/closing part 11 and supporter opening/closing part 21, imaging target (generally a patient) easier. For example, when upper direction is set as 0 degree with reference to FIG. 3, in order that supporter opening/closing part 21 and rotator opening/closing part 11 are integrally moved in a circumferential direction and opened and a patient passes one side of imaging apparatus 100 and is set at the center thereof, the predetermined angle at which rotator opening/closing part 11 and supporter opening/closing part 21 are formed may be a range between 45 to 135 degrees or a range between 225 to 315 degrees.

In addition, referring to FIG. 1 to FIG. 4, rotator 1 may further include a rotator fixing part 12 which forms the perforated circular plate shape together with rotator opening/closing part 11 before rotator opening/closing part 11 is separated along the direction of rotating axis 10. That is, one perforated circular plate may be formed by combining rotator opening/closing part 11 and rotator fixing part 12 together. Rotator fixing part 12 is relatively fixed to rotator opening/closing part 11 even when rotator opening/closing part 11 moves to separate so as to open one side of imaging apparatus 100. However, rotator fixing part 12 is not fixed to supporter 2. That is, rotator opening/closing part 11 and rotator fixing part 12 rotates to supporter 2.

Figure 5:
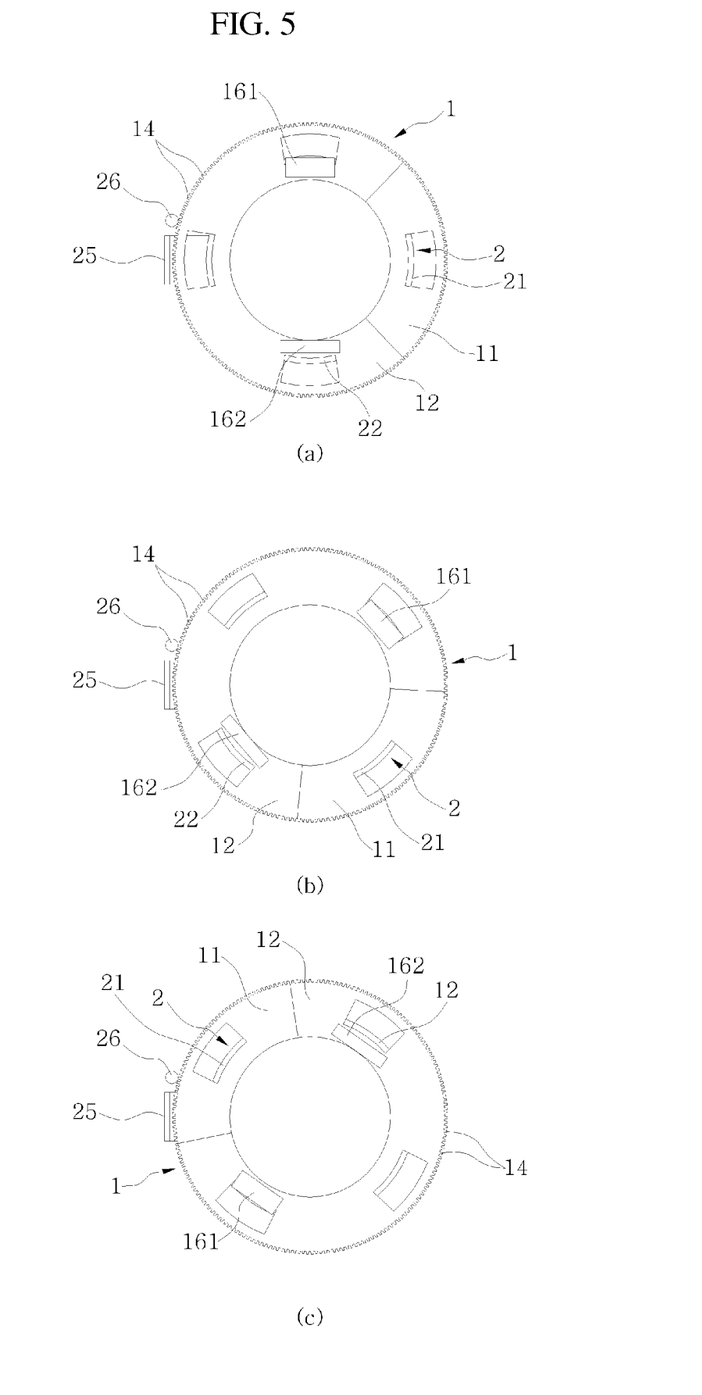
FIG. 5 is a schematic view showing an example of rotation of a rotator.

FIG. 5 is a schematic view showing an example of rotation of a rotator.

In addition, referring to FIG. 1 to FIG. 4, rotator 1 may further include a source 161 emitting light (which may also be referred to as an "imaging source"), and a detector 162 receiving light (which may also be referred to as an "an imaging detector"). Source 161 and detector 162 may be arranged to face each other such that rotating axis 10 is disposed at the center therebetween.

As an example, referring to FIG. 1 and FIG. 3, source 161 may be disposed at one portion (upper portion as shown in FIG. 1 and FIG. 3) of the other side of rotator 1, and detector 162 may be disposed at the other portion (lower portion as shown in FIG. 1 and FIG. 3) of the other side of rotator 1. As such, since source 161 and detector 162 are disposed to face one another at both sides of the perforated center portion of rotator 1, emission of light can be performed in a state that an imaging object which will be photographed or imaged is set at the perforated center portion of rotator 1. At this time, rotator 1 rotates as shown in FIG. 5, so three-dimensional image as well as two-dimensional image can be taken.

At this time, light emitted from source 161 may be light having X-ray wavelength. That is, source 161 emits X-ray beam, and detector 162 may receive X-ray beam. By using X-ray beam, imaging apparatus 100 according to an embodiment of the present invention may be used to two-dimensional or three-dimensional CT (Computed Tomography).

In addition, as shown in FIG. 1 to FIG. 4, rotator 1 may include a rotating gear 14 which is formed on outer circumference thereof along a circumferential direction. Rotating gear 14 is engaged with a rotating motor 26 of supporter 2 which will be explained later, and rotator 1 rotates around rotating axis 10 as shown in FIG. 5 if rotating motor 26 operates. For example, rotating gear 14 may be spur & pinion gear.

Figure 6:
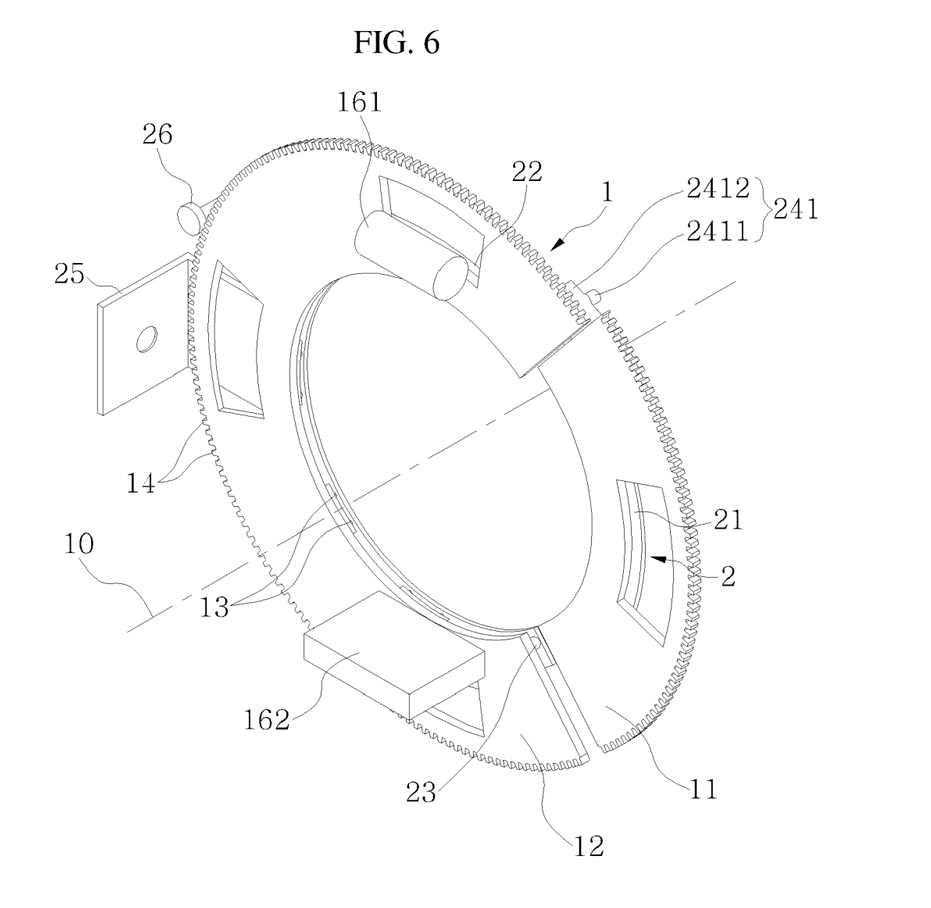
FIG. 6 is a schematic frontal perspective view of state in that a rotator opening/closing part and a supporter opening/closing part are separated in a direction of a rotating axis by a lifter.
Figure 7:
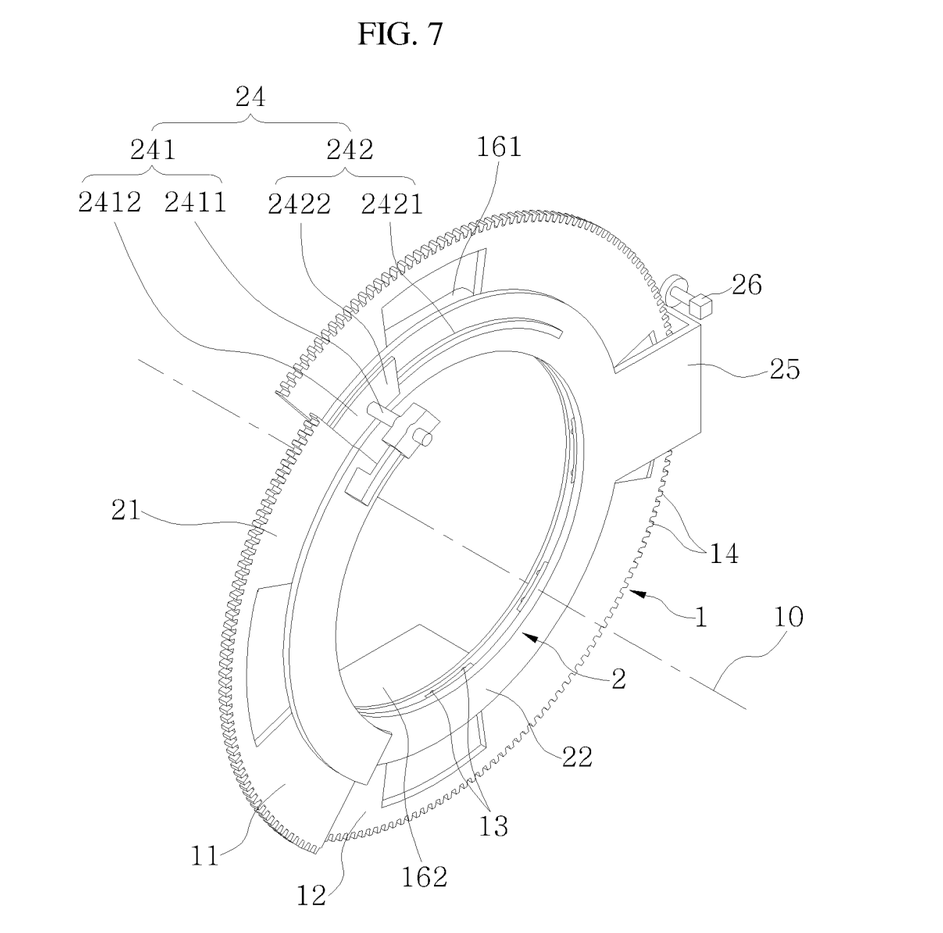
FIG. 7 is a schematic rear perspective view of state in FIG. 6.

FIG. 6 is a schematic frontal perspective view of state in that a rotator opening/closing part and a supporter opening/closing part are separated in a direction of a rotating axis by a lifter, and FIG. 7 is a schematic rear perspective view of state in FIG. 6.

Further, referring to FIG. 1, FIG. 2, FIG. 6 and FIG. 7, for relative rotation of rotator 1 with respect to supporter 2, a rolling device may be provided along a rotation direction between rotator 1 and supporter 2. For example, rotator 1 may be provided with a guide roller 13 along a circumferential direction, and supporter 2 may be provided with a rotating guide 23 which forms a path for rolling movement of guide roller 13 along a circumferential direction.

That is, supporter 2, as partially shown in FIG. 6, may further include rotating guide 23 which is formed on the other side thereof along a circumferential direction such that rotator 1 can rotate around rotating axis 10, rotator 1 may further include guide roller 13 which is provided along a circumferential direction responding to rotating guide 23 at one side thereof. To the contrary, rotating guide 23 may be provided to rotator 1, and guide roller 13 may be provided to the supporter 2. However, it is preferable that guide roller 13 which is rolling device is provided to rotator 1 which actually rotates. Further, for example, rotating guide 23 may have a shape of a rail forming a path, and guide roller 13 may have a shape engaging with the rail.

Subsequently, supporter 2 will be explained.

Referring to FIG. 1 to FIG. 4, supporter 2 has a shape of a perforated circular plate, and the other side thereof is connected to one side of rotator 1 such that movement of rotator 1 is restricted only to rotation movement. The shape of the perforated circular plate may be a shape of a circular plate which is perforated with a circle shape at a center portion thereof, a shape of alphabet O, or the like.

For example, the perforated circular plate shape of supporter 2, as shown in FIG. 1 to FIG. 4, may be formed such that an inner diameter is similar to rotator 1 and an outer diameter is less than rotator 1. Relative size of supporter 2 with respect to rotator 1 may be determined such that supporter 2 may have strength covering weight of rotator 1, vibration due to rotation, unexpected impact, operational load by manipulation of supporter 2 through an manipulator, and the like.

Figure 8:
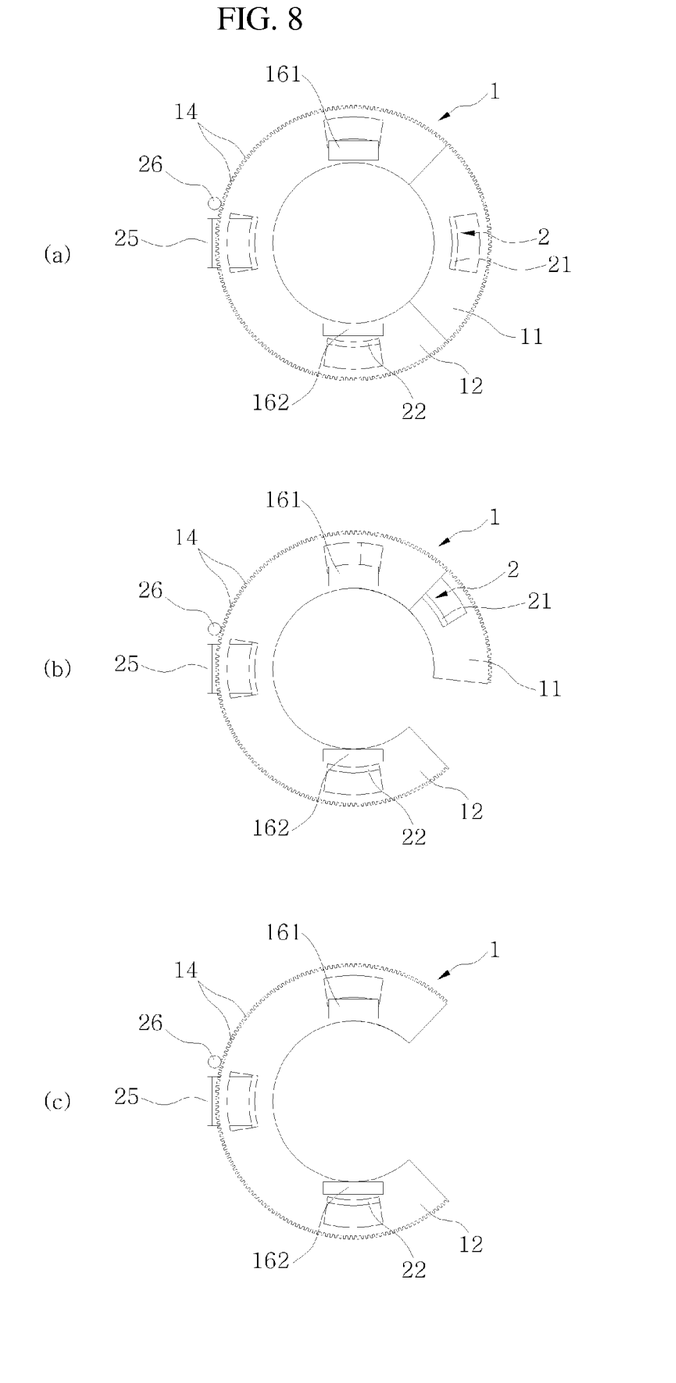
FIG. 8 is a front elevational view showing steps of processes in which a rotator opening/closing part and a supporter opening/closing part move along an opening/closing guide.
Figure 9:
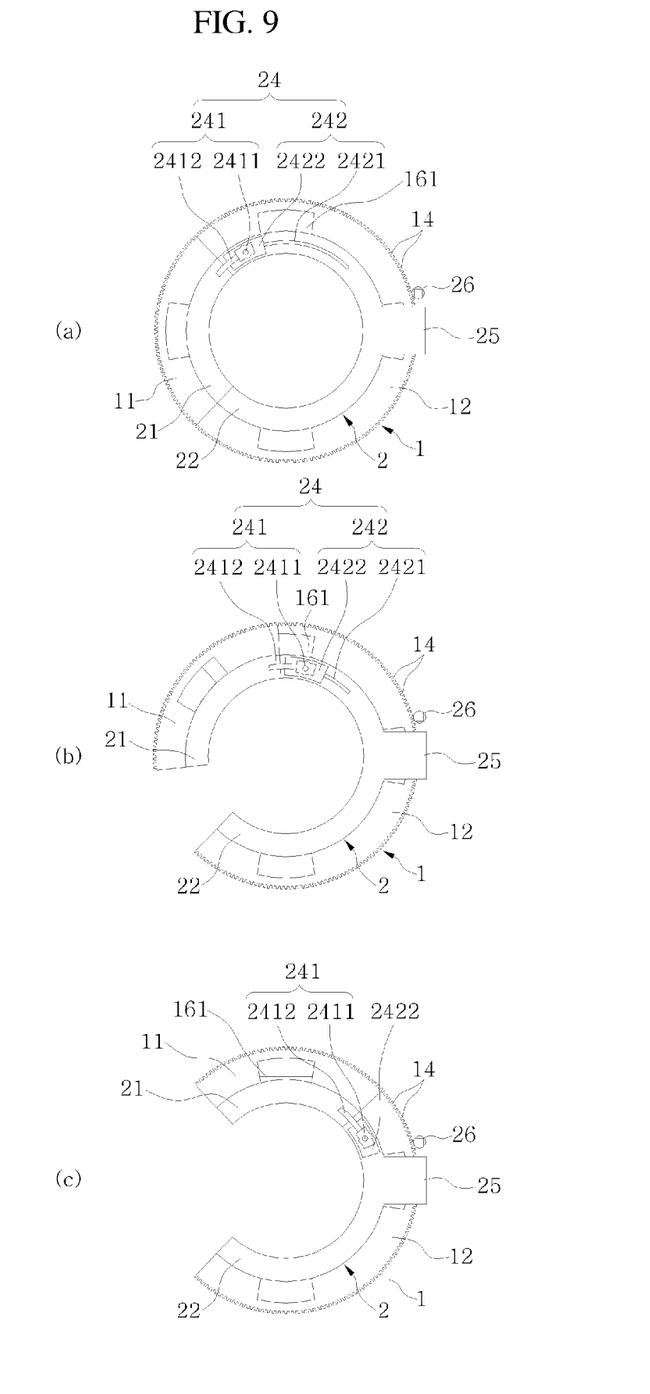
FIG. 9 is a rear elevational view showing steps of processes of FIG. 8.

FIG. 8 is a front elevational view showing steps of processes in which a rotator opening/closing part and a supporter opening/closing part move along an opening/closing guide, and FIG. 9 is a rear elevational view showing steps of processes of FIG. 8.

Referring to FIG. 6 to FIG. 9, supporter 2 includes supporter opening/closing part 21 a part of which is separated along rotating axis 10 and then rotates by a predetermined angle around rotating axis 10. Here, the predetermined angle may be an angle by which the side of imaging apparatus 100 can be opened in which imaging object can be easily moved and set.

As an example, supporter opening/closing part 21 which corresponds to a part of supporter 2 may be a part corresponding to rotator opening/closing part 11 in supporter 2. That is, supporter opening/closing part 21 may be a part of supporter 2 which overlaps with rotator opening/closing part 11 in a direction of rotating axis 10. As such, since supporter opening/closing part 21 and rotator opening/closing part 11 are formed to be overlapped at the same position, both opening/closing parts 11 and 21 can integrally open the side of imaging apparatus 100 by a opening/closing module 24 which will be explained later.

As an example, referring to (a) of FIG. 8 and FIG. 9, supporter opening/closing part 21 is arranged to overlap with rotator opening/closing part 11 approximately in a range of 90 degrees and to integrally operate with rotator opening/closing part 11. In addition, referring to (c) of FIG. 8 and FIG. 9, angle of rotation movement of supporter opening/closing part 21 and rotator opening/closing part 11 are approximately 90 degrees. That is, in an embodiment of the present invention, the predetermined angle of rotation movement of supporter opening/closing part 21 is approximately set at 90 degrees. However, this is an exemplary embodiment of the present, and it can be various determined depending on conditions to which imaging apparatus 100 is applied.

Further, supporter 2 may further include a supporter fixing part 22 which forms the perforated circular plate together with supporter opening/closing part 21 before supporter opening/closing part 21 is separated along a direction of rotating axis 10. That is, by combination of supporter opening/closing part 21 and supporter fixing part 22, one perforated circular plate can be obtained. Supporter fixing part 22 is relatively fixed with respect to supporter opening/closing part 21 even when supporter opening/closing part 21 is separated to move so as to open one side of imaging apparatus 100.

In addition, supporter 2 may further include rotating motor 26 which is engaged with rotating gear 14 to urge rotator 1 to rotate around rotating axis 10. Although the shape of rotating motor 26 is schematically shown in the drawing, rotating motor 26 is provided with a driving part which can be engaged with the rotating gear 14 via female/male engagement or the like. While rotating gear 14 rotates by driving of rotating motor 26, rotator 1 rotates around rotating axis 10. In addition, rotating motor 26 needs not to be necessarily mounted to supporter 2, but may be mounted other part which can be fixed.

Further, as shown in FIG. 1 to FIG. 4, supporter 2 may further include a manipulator connecting part 25 which is connected to a manipulator which controls linear or rotational movement in space. Manipulator is not shown in the drawing, but may be generally understood as a device for controlling radioactive device at a remote safe place. And it is configured to control the device by various freedom degrees by electrical and mechanical mechanisms. Manipulator connecting part 25 is formed on supporter 2 such that supporter 2 can be controlled by such manipulator.

For example, referring to FIG. 1 and FIG. 2, manipulator connecting part 25 may be formed by extending in a radial direction from one portion (left portion in FIG. 1 and right portion in FIG. 2) of supporter 2 and then bending along rotating axis 10 and further extending. In addition, considering moving and setting of an imaging object, as shown in FIG. 1 to FIG. 4, manipulator connecting part 25 may be formed on opposite side of a portion where supporter opening/closing part 21 is formed. Such manipulator connecting part 25 may be varied to various shapes depending on surroundings to which imaging apparatus 100 is applied.

Meanwhile, referring to FIG. 2, FIG. 4, FIG. 7 and FIG. 9, supporter 2 may further include opening/closing module 24 which separates and rotates supporter opening/closing part 21. As described above, supporter opening/closing part 21 may be separated from supporter fixing part 22 along a direction of rotating axis 10 and then can rotate by a predetermined angle around rotating axis 10. Opening/closing module 24 may be provided such that separation and rotation of supporter opening/closing part 21 can be performed.

Opening/closing module 24 may include a lifting part 241 which separates supporter opening/closing part 21 along a direction of rotating axis 10, and a rotating part 242 which rotates supporter opening/closing part 21 by a predetermined angle around rotating axis 10. That is, supporter opening/closing part 21 and rotator opening/closing part 11 which is operated together are lifter in a direction of rotating axis 10 by lifting part 241. Subsequently, while supporter opening/closing part 21 and rotator opening/closing part 11 which have been lifted by rotating part 242 rotates, the side of imaging apparatus 100 is opened by a predetermined angle.

Further, referring to FIG. 2, FIG. 4, FIG. 7 and FIG. 9, rotating part 242 may include an opening/closing guide 2421 which is formed at one side of supporter fixing part 22 along a circumferential direction, and a moving member 2422 which moves along opening/closing guide 2421.

Lifting part 241 may include a guide rod 2411 which protrudes from moving member 2422 along a direction of rotating axis 10, and a connecting member 2412 one end of which is connected to one side of supporter opening/closing part 21 and the other end of which is penetrated so as to be moved along a longitudinal direction of guide rod 2411.

That is, connecting member 2412 moves along a longitudinal direction of guide rod 2411 being protruded from moving member 2422, so supporter opening/closing part 21 and rotator opening/closing part 11 one sides of which are connected to one end of connecting member 2412 are integrally lifted from the state of FIG. 2 to the state of FIG. 7. At this time, not shown in the drawing, lifting part 241 may further include an air cylinder which urges connecting member 2412 to move along a longitudinal direction of guide rod 2411. Operation of lifting of lifting part 241 may be preformed by the air cylinder.

Further, moving member 2422 moves along opening/closing guide 2421, so connecting member 2412 which is penetrated by guide rod 2411 being protruded from moving member 2422 to be connected thereto also moves, and supporter opening/closing part 21 and rotator opening/closing part 11 one sides of which are connected to one end of connecting member 2412 are integrally moved from the state of (a) of FIG. 9 to the state of (c) via the state of (b).

At this time, not shown in the drawing, moving member 2422 may include an opening/closing gear which is formed on an outer circumference or an inner circumference along a circumferential direction, and rotating part 242 may further include an opening/closing motor which is engaged with the opening/closing gear to urge moving member 2422 to move along opening/closing guide 2421. As an example, the opening/closing gear is formed by a spur & pinion gear, similar to the principle of rotation of rotator 1 with respect to supporter 2, to be rotated by the opening/closing motor, thereby urging moving member 2422 to move along opening/closing guide 2421. At this time, in order that the opening/closing gear which is formed moving member 2422 along a circumferential direction is engaged with the opening/closing motor to move moving member 2422 farther, length of moving member 2422 in a circumferential direction can be formed to be longer than that shown in the drawing.

Further, a roller is attached to moving member 2422, similar to guide roller 13 of rotator 1, so as to move while riding opening/closing guide 2421.

Hereinafter, based on the above-stated description, rotation of rotator 1 with respect to supporter 2 and operation of integral conversion of rotator opening/closing part 11 and supporter opening/closing part 21 by opening/closing module 24 will be briefly explained.

First, regarding rotational movement of rotator 1 with respect to supporter 2, in the aspect of driving force, rotating gear 14 which is formed on the outer circumference of rotator 1 rotates while being engaged with rotating motor 26 of supporter 2, and thereby rotator 1 rotates. And, at the aspect of movement path, guide roller 13 which is provided to rotator 1 moves along a path of rotating guide 23 which is provided to supporter 2, and thereby rotational movement of rotator 1 is accomplished.

Further, supporter 2 restricts linear movement or rotational movement of rotating guide 23 along other directions, except the rotational movement along the path, so as to perform a role of supporting rotator 1. In order for supporter 2 to perform this function, not shown in the drawing, a groove may be formed along rotating guide 23 and a protrusion which is coupled to the groove is formed on guide roller 13, so movement of rotator 1 along a direction of rotating axis 10 can be prevented.

Subsequently, regarding the operation of integral conversion of rotator opening/closing part 11 and supporter opening/closing part 21 by opening/closing module 24, at the aspect of driving force, not shown in the drawing, the opening/closing gear which is formed on connecting member 2412 rotates while being engaged with the opening/closing motor, integral opening/closing operation of rotator opening/closing part 11 and supporter opening/closing part 21 can be performed. And at the aspect of movement path, the roller which is provided to connecting member 2412 moves along the path of opening/closing guide 2421 which is provided to supporter 2, so integral opening/closing operation of rotator opening/closing part 11 and supporter opening/closing part 21 can be performed.

According to an embodiment of the present invention, rotator 1 is formed at a shape of a symmetrical perforated circular plate (alphabet O shape), so vibration during rotation can be reduced, and thickness and width can be slim so occupied space can be reduced so that space for an imaging object which will be photographed can be increased.

Further, since rotator opening/closing part 11 and supporter opening/closing part 21 are provided, sides of rotator 1 and supporter 2 can be selectively opened and closed, so setting of the imaging object which will be photographed can be easily performed through the opened side space.

Meanwhile, opening/closing module 24 which is included in according to an embodiment of the present invention imaging apparatus 100 will be described as embodiment of the present invention, with reference to imaging apparatus 100. The same reference numerals will be used for the same element as opening/closing module 24 which is included in imaging apparatus 100, and repeated explanation will be briefly made or omitted. An embodiment of opening/closing module 24 will be described with reference to FIG. 1 to FIG. 9 as an embodiment which is applied to imaging apparatus 100 according to an embodiment of the present invention.

Referring to FIG. 1 to FIG. 9, opening/closing module 24 according to an embodiment of the present invention includes lifting part 241 which separates an opening/closing part 21 in a direction of rotating axis 10, and rotating part 242 which rotates opening/closing part 21 by a predetermined angle around rotating axis 10. At this time, opening/closing part 21 corresponds to supporter opening/closing part 21 of imaging apparatus 100 according to an embodiment of the present invention, and has been indicated by the same reference numeral.

Rotating part 242 may include opening/closing guide 2421 which is formed on one side of a fixing part 22 along a circumferential direction, and moving member 2422 which moves along opening/closing guide 2421, and lifting part 241 may include guide rod 2411 which protrudes from moving member 2422 in a direction of rotating axis 10, and connecting member 2412 one end of which is connected to one side of opening/closing part 21 and the other end of which is penetrated so as to be able to move along a longitudinal direction of guide rod 2411. At this time, fixing part 22 is an element corresponding to supporter fixing part 22 of imaging apparatus 100 according to an embodiment of the present invention and has been indicated by the same reference numeral.

Moving member 2422 may include an opening/closing gear which is formed on an inner circumference or an outer circumference along a circumferential direction.

Rotating part 242 may further include an opening/closing motor which is engaged with the opening/closing gear to urge moving member 2422 to move along opening/closing guide 2421.

Lifting part 241 may further include an air cylinder which urges connecting member 2412 to move in a longitudinal direction of guide rod 2411.

Meanwhile, a control method S100 for an opening/closing module according to an embodiment of the present invention which is a control method for opening/closing module 24 according to an embodiment of the present invention will be described hereinafter. For ease of description, the same reference numerals will be used for the same elements with opening/closing module 24 and the repeated description will be briefly made or omitted.

Figure 10:
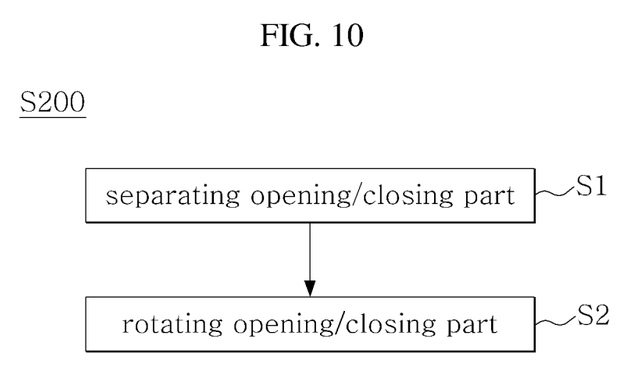
FIG. 10 is a flow chart of a control method for an opening/closing module according to an embodiment of the present invention.

FIG. 10 is a flow chart of a control method for an opening/closing module according to an embodiment of the present invention.

Referring to FIG. 10, control method S100 according to an embodiment of the present invention is a control method for controlling an opening/closing module including lifting part 241 which separates opening/closing part 21 along a direction of rotating axis 10, and rotating part 242 which rotates opening/closing part 21 around rotating axis 10, and includes a step S1 of separating opening/closing part 21 in a direction of rotating axis by lifting part 241, and a step S2 of rotating the separated opening/closing part 21 by a predetermined angle around rotating axis 10 by rotating part 242.

Rotating part 242 may include opening/closing guide 2421 which is formed on one side of fixing part 22 along a circumferential direction, and moving member 2422 which moves along opening/closing guide 2421, and lifting part 241 may include guide rod 2411 which is protruded from moving member 2422 in a direction of rotating axis 10, and connecting member 2412 one end of which is connected to one side of opening/closing part 21 and the other end of which is penetrated so as to be able to move along a longitudinal direction of guide rod 2411.

Further, moving member 2422 may include an opening/closing gear which is formed on an outer circumference or an inner circumference along a circumferential direction, rotating part 242 may further include an opening/closing motor which is engaged with the opening/closing gear to urge moving member 2422 to move along opening/closing guide 2421, and lifting part 241 may further include an air cylinder which urges connecting member 2412 to move in a longitudinal direction of guide rod 2411.

Accordingly, step of separating S1 may be a step of moving connecting member 2412 which is connected to opening/closing part 21 via air cylinder along a longitudinal direction of guide rod 2411 so as to separate opening/closing part 21 in a direction of rotating axis 10. And step of rotating S2 may be a step that opening/closing part 21 rotates together with guide rod 2411 and connecting member 2412 while moving member 2422 moves along opening/closing guide 2421 by the operation of opening/closing motor which is engaged with opening/closing gear.

Further, control method S100 for opening/closing module according to an embodiment of the present invention may include step S1 of separating opening/closing part 21 in a direction of rotating axis by lifting part 241, and step which is opposite to step S2 of rotating separated opening/closing part 21 by a predetermined angle around rotating axis 10 by rotating part 242. That is, control method S100 for opening/closing module may include step of rotating opening/closing part 21 to turn back to a position from which opening/closing part 21 was separated, and step of moving opening/closing part 21 in a direction of rotating axis to re-couple to fixing part 22.

As an example, through control method S100 for opening/closing module, supporter 2 and rotator 1 of imaging apparatus 100 can freely convert between shapes of O-shape in which side is closed and C-shape in which side is opened. Further, through this conversion, a patient can be easily moved through the opened side, and after a patient is moved to the center of imaging apparatus 100, the side is closed and examination is performed.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

According to the present invention, since rotator is formed by a symmetrical perforated circular plate (alphabet O shape), vibration during rotation can be reduced, and thickness and width can be slim so occupied space can be reduced so that space for an imaging object which will be photographed can be increased.

Further, since rotator opening/closing part and supporter opening/closing part are provided, sides of rotator and supporter can be selectively opened or closed, so setting of an imaging object which will be photographed can be easily performed through opened side space.

What is claimed is:

1. An imaging apparatus comprising:
    a rotator having a shape of a perforated circular plate and rotating around a rotating axis of a center of the perforated circular plate shape, the rotator having an imaging source and an imaging detector for imaging an imaging object; and
    a supporter having a perforated circular plate and one side of which is connected to one side of the rotator such that in a position of the supporter, the rotator is restricted only to rotation movement,
    wherein the supporter includes a supporter opening/closing part a part of which is separated along the rotating axis and then rotates by a predetermined angle around the rotating axis, and
    the rotator includes a rotator opening/closing part a part of which integrally moves with the supporter opening/closing part.

2. The imaging apparatus of claim 1, wherein the rotator opening/closing part is a portion corresponding to a range of a predetermined angle in a circumferential direction in the rotator, and the supporter opening/closing part is a portion in the supporter corresponding to the rotator opening/closing part.

3. The imaging apparatus of claim 1, wherein the supporter further comprises a supporter fixing part which forms the perforated circular plate of the supporter together with the supporter opening/closing part before the supporter opening/closing part is separated along a direction of the rotating axis,
    and the rotator further comprises a rotator fixing part which forms the perforated circular plate shape of the rotator together with the rotator opening/closing part before the rotator opening/closing part is separated along a direction of the rotating axis.

4. An imaging apparatus comprising:
    a rotator having a shape of a perforated circular plate and rotating around a rotating axis of a center of the perforated circular plate shape, the rotator including a source emitting light and a detector receiving the light to image an imaging object, and the source and the detector are arranged to face each other such that the rotating axis is disposed at the center therebetween; and
    a supporter having a perforated circular plate and one side of which is connected to one side of the rotator such that in a position of the supporter, the rotator is restricted only to rotation movement,
    wherein the supporter includes a supporter opening/closing part a part of which is separated along the rotating axis and then rotates by a predetermined angle around the rotating axis, and
    the rotator includes a rotator opening/closing part a part of which integrally moves with the supporter opening/closing part.

5. The imaging apparatus of claim 1, wherein the rotator comprises a rotating gear which is formed on an outer circumference of the rotator along a circumferential direction.

6. The imaging apparatus of claim 5, wherein the supporter further comprises a rotating motor which is engaged with the rotating gear to rotate the rotator around the rotating axis.

7. The imaging apparatus of claim 1, wherein the supporter further comprises a rotating guide which is formed on another side of the supporter along a circumferential direction such that the rotator can rotate around the rotating axis,
    and the rotator further comprises a guide roller which is provided at one side of the rotator along a circumferential direction corresponding to the rotating guide.

8. The imaging apparatus of claim 1, wherein the supporter further comprises a manipulator connecting part which is connectable to a manipulator which controls linear or rotational movement in space.

9. The imaging apparatus of claim 3, wherein the supporter further comprises an opening/closing module which separates and rotates the supporter opening/closing part.

10. The imaging apparatus of claim 9, wherein the opening/closing module comprises:
    a lifting part which separates the supporter opening/closing part along a direction of the rotating axis; and
    a rotating part which rotates the supporter opening/closing part by a predetermined angle around the rotating axis.

11. The imaging apparatus of claim 10, wherein the rotating part comprises an opening/closing guide which is formed at one side of the supporter fixing part along a circumferential direction, and a moving member which moves along the opening/closing guide,
    and the lifting part comprises a guide rod which protrudes from the moving member along a direction of the rotating axis, and a connecting member one end of which is connected to one side of the supporter opening/closing part and another end of the connecting member is penetrated so as to be moved along a longitudinal direction of the guide rod.

12. The imaging apparatus of claim 11, wherein the moving member comprises an opening/closing gear which is formed on an outer circumference or an inner circumference along a circumferential direction.

13. The imaging apparatus of claim 12, wherein the rotating part further comprises an opening/closing motor which is engaged with the opening/closing gear to urge the moving member to move along the opening/closing guide.

14. The imaging apparatus of claim 11, wherein the lifting part further comprises an air cylinder which moves the connecting member along a longitudinal direction of the guide rod.

15. An imaging apparatus comprising:
a rotator having a shape of a perforated circular plate and rotating around a rotating axis of a center of the perforated circular plate shape, the rotator for supporting an imaging source and an imaging detector for imaging an imaging object; and
a supporter having a perforated circular plate and one side of which is connected to one side of the rotator such that in a position of the supporter, the rotator is restricted only to rotation movement,
wherein the supporter includes a supporter opening/closing part a part of which is separated along the rotating axis and then rotates by a predetermined angle around the rotating axis,
and the rotator includes a rotator opening/closing part a part of which integrally moves with the supporter opening/closing part.

* * * * *